United States Patent
Ko et al.

(10) Patent No.: US 8,228,502 B2
(45) Date of Patent: Jul. 24, 2012

(54) MEASUREMENT DEVICE EQUIPPED WITH DEVICE FOR DECIDING MEASUREMENT START POINT

(75) Inventors: Hyunsung Ko, Seoul (KR); Chul Huh, Daejeon (KR); Kyung Hyun Kim, Daejeon (KR); Wanjoong Kim, Goyang-si (KR); Bong Kyu Kim, Daejeon (KR); Gun Yong Sung, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 288 days.

(21) Appl. No.: 12/545,170

(22) Filed: Aug. 21, 2009

(65) Prior Publication Data

US 2010/0157295 A1 Jun. 24, 2010

(30) Foreign Application Priority Data

Dec. 22, 2008 (KR) .................. 10-2008-0131063

(51) Int. Cl.
*G01J 3/28* (2006.01)
(52) U.S. Cl. ..... 356/326; 356/445; 356/432; 422/82.01; 422/82.05; 422/82.09
(58) Field of Classification Search .............. 356/326, 356/445, 432; 422/82.01, 82.05, 82.09, 82.11, 422/82.08
See application file for complete search history.

(56) References Cited

U.S. PATENT DOCUMENTS

| | | | |
|---|---|---|---|
| 6,134,003 A | 10/2000 | Tearney et al. | |
| 7,023,544 B2 | 4/2006 | Cunningham et al. | |
| 7,118,916 B2 | 10/2006 | Matzinger | |
| 7,292,336 B2 | 11/2007 | Cunningham et al. | |
| 7,889,348 B2 * | 2/2011 | Tearney et al. | 356/451 |
| 7,927,822 B2 * | 4/2011 | Genick et al. | 435/7.2 |
| 2003/0138962 A1 | 7/2003 | Katayama et al. | |
| 2004/0223881 A1 | 11/2004 | Cunningham et al. | |
| 2007/0172894 A1 | 7/2007 | Genick et al. | |

FOREIGN PATENT DOCUMENTS

| | | |
|---|---|---|
| JP | 56-168148 | 12/1981 |
| JP | 6-72849 | 3/1994 |
| JP | 2001-108525 | 4/2001 |

(Continued)

OTHER PUBLICATIONS

Mateus, Carlos F.R. et al., "Compact Label-Free Biosensor Using VCSEL-Based Measurement System," *IEEE Photonics Technology Letters*, vol. 16(7):1712-1714 (2004).

*Primary Examiner* — Gregory J Toatley
*Assistant Examiner* — Iyabo S Alli
(74) *Attorney, Agent, or Firm* — Nelson Mullins Riley & Scarborough LLP; EuiHoon Lee, Esq.

(57) ABSTRACT

Provided is a measurement device. The measurement device includes a sensor, a wavelength-tunable light source, an additional light source, a coupler, and an optical power measurer. The sensor accepts a sample. The wavelength-tunable light source irradiates wavelength-tunable light to detect a reaction of the sensor. The additional light source irradiates wavelength-fixed light to detect an initial time of the reaction. The coupler combines the wavelength-tunable light source and the additional light source and irradiates the combined input light on the sensor. The optical power measurer detects the reaction of the sensor from an output light transmitted through or reflected by the sensor.

15 Claims, 21 Drawing Sheets

FOREIGN PATENT DOCUMENTS

| | | |
|---|---|---|
| JP | 2003-169700 | 6/2003 |
| JP | 2004-144750 | 5/2004 |
| JP | 2006-505788 | 2/2006 |
| JP | 2008-203216 | 9/2008 |
| KR | 1020080084030 | 9/2008 |
| WO | 04/044560 A1 | 5/2004 |

* cited by examiner

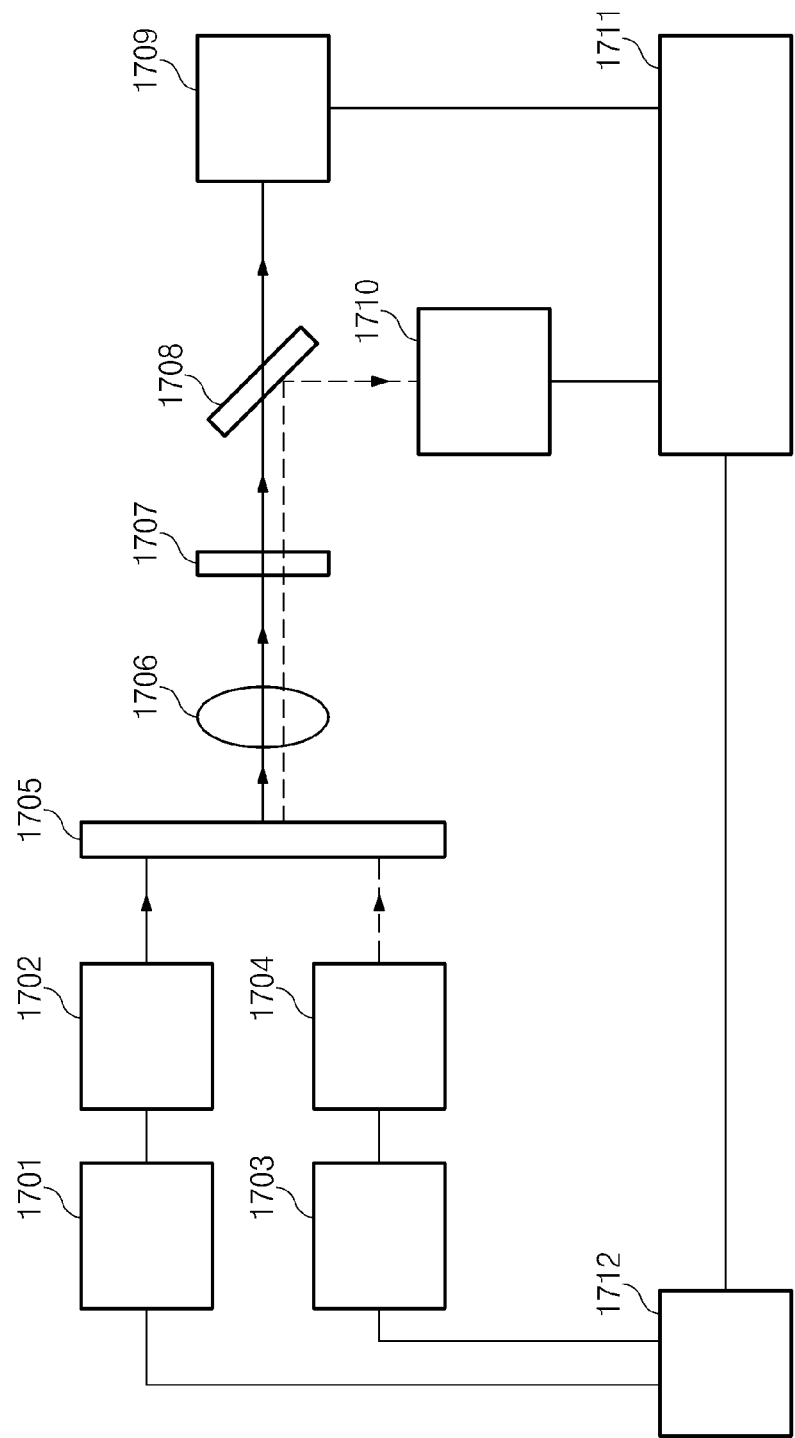

ated in and constitute a part of this specification. The drawings
MEASUREMENT DEVICE EQUIPPED WITH DEVICE FOR DECIDING MEASUREMENT START POINT

CROSS-REFERENCE TO RELATED APPLICATIONS

This U.S. non-provisional patent application claims priority under 35 U.S.C. §119 of Korean Patent Application No. 10-2008-0131063, filed on Dec. 22, 2008, the entire contents of which are hereby incorporated by reference.

BACKGROUND OF THE INVENTION

The present invention disclosed herein relates to a biosensor, and more particularly, to a biosensor measurement device including a device for deciding a measurement start point.

Optical biosensor measurement devices are devices that detect a specific antibody using a biosensor to which the specific antibody is fixed. When blood plasma or other liquid samples including an antigen is inputted into a biosensor including a specific antigen, the antibody fixed in the biosensor is combined with the antigen in the liquid samples to change the optical characteristics of the optical biosensor. The optical biosensor measurement device measures whether or not a specific antigen exists and if so, the concentration of the antigen by comparing transmittance and reflectance of a biosensor before an antigen-antibody reaction and transmittance and reflectance of the biosensor after the antigen-antibody reaction.

SUMMARY OF THE INVENTION

The present invention provides a sensor chip and a sensor measurement device for measuring a time point when a sample contacts a sensor.

Embodiments of the present invention provide measurement devices including: a sensor accepting a sample; a wavelength-tunable light source irradiating wavelength-tunable light to detect a reaction of the sensor; an additional light source irradiating wavelength-fixed light to detect an initial time of the reaction; a coupler combining the wavelength-tunable light source and the additional light source and irradiating the combined input light on the sensor; and an optical power measurer detecting the reaction of the sensor from an output light transmitted through or reflected by the sensor.

In some embodiments, the additional light source may have optical power varied with time.

In other embodiments, the wavelength-tunable light source may have optical power constant with time.

In still other embodiments, the measurement device may further include a wavelength light source regulator controlling a wavelength output of the wavelength-tunable light source.

In even other embodiments, the measurement device may further include a light source regulator modulating an output power of the additional light source into a sine wave or a square wave.

In yet other embodiments, the measurement device may further include a signal processing unit separating a component of the additional light source from a result of the detection of the optical power measurer.

In further embodiments, the sensor may include a specific antibody for detecting the reaction of the sensor.

In still further embodiments, the sample may include an antigen reacting with the antibody.

In even further embodiments, the measurement device may further include a lens changing the combined input light into parallel light.

In yet further embodiments, the sensor may include an optical biosensor.

In other embodiments of the present invention, measurement devices include: a sensor accepting a sample; a light source irradiating light to the sensor; a beam splitter dividing output light transmitted through or reflected by the sensor into two branches; a spectroscope detecting a reaction of the sensor by receiving one branched output light from the beam splitter; and an optical power measurer detecting an initial reaction time of the sensor by receiving the other branched output light from the beam splitter.

In some embodiments, the optical power measurer may include an optical filter outputting a wavelength band according to the reaction in the other branched output light.

In other embodiments, the wavelength band may include a wavelength having maximum transmittance or reflectance and wavelengths adjacent thereto.

In still other embodiments, the optical filter may include a band pass filter.

In even other embodiments, the sensor may include an optical biosensor.

BRIEF DESCRIPTION OF THE FIGURES

The accompanying figures are included to provide a further understanding of the present invention, and are incorporated in and constitute a part of this specification. The drawings illustrate exemplary embodiments of the present invention and, together with the description, serve to explain principles of the present invention. In the figures:

FIG. 17A is a diagram illustrating an optical biosensor measurement device according to a second embodiment;

DETAILED DESCRIPTION OF PREFERRED EMBODIMENTS

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Hereinafter, exemplary embodiments of the present invention will be described in detail with reference to the accompanying drawings.

Figure 1:
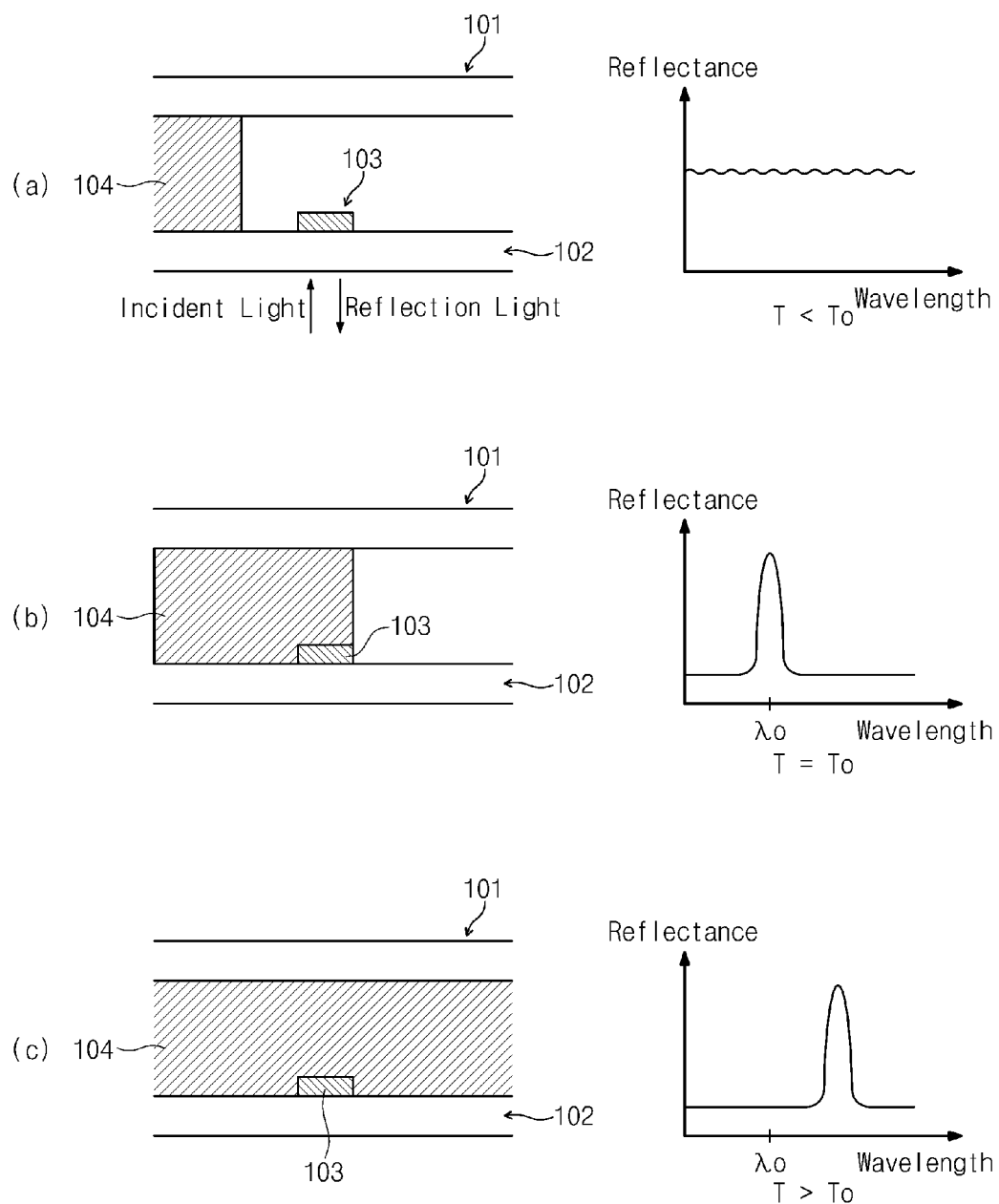
FIG. 1 is a diagram illustrating a biosensor chip and optical characteristics of an optical biosensor by an antigen-antibody reaction.

FIG. 1 is a diagram illustrating a variation of optical characteristics of a sensor before and after a liquid sample contacts the sensor for measuring the sample.

Referring to FIG. 1, a sample 104 includes a liquid such as blood plasma and blood including a specific antigen. The sample is in a fluid state (for example, liquid or gas). A biosensor 103 includes an antibody to the specific antigen.

The biosensor causes an antigen-antibody reaction with a target antigen in the sample 104. The biosensor 103 may be fixed on an upper plate 101 or a lower plate 102 of a biosensor chip. The lower plate 102 of the biosensor chip is covered with the upper plate 101 of the biosensor chip. Also, the biosensor chip may not include the upper plate 101 when measuring a reflection light.

The biosensor chip may include a channel to allow the sample 104 to flow into the biosensor 103. The upper plate 101 of the biosensor chip may be excluded according to the design of the biosensor chip. The sample 104 includes an antigen reacting with the biosensor 103. The lower plate 102 of the biosensor chip is transparent enough to transmit an incident light. The biosensor 103 may include a structure of generating a peak or a dip in a reflectance spectrum or a transmittance spectrum according to a refractive index of a contact material.

FIG. 1(a) shows a reflectance spectrum before the contact of the sample 104 and the biosensor. A space between the upper plate 101 and the lower plate 102 of the biosensor chip are filled with air or other fluids before the sample 104 contacts the biosensor 103. The reflectance spectrum does not have a peak for the refractive index of the above fluid.

As illustrated in FIG. 1(b), when the sample 104 contacts the biosensor 103, the refractive index of a material filling the space between the upper plate 101 and the lower plate 102 of the biosensor chip is changed. When the refractive index of the material a value within a specific range, a peak is generated in the reflectance spectrum of the biosensor chip.

As illustrated in FIG. 1(c), when the sample 104 continuously flows on the biosensor 103, membranes generated from the continuous combination of an antigen and antibody are piled on the biosensor 103. With the continuously piled membranes, the structure of the biosensor 103 is changed to cause a change of a reflectance peak of the biosensor.

With the antigen-antibody reaction, the peak wavelength may be increased or decreased according to the biosensor chip. Embodiments will not be limited to the antigen-antibody reaction. That is, all the measurement devices including a material capable of reacting with a sample can be applied to this embodiment.

Figure 2:
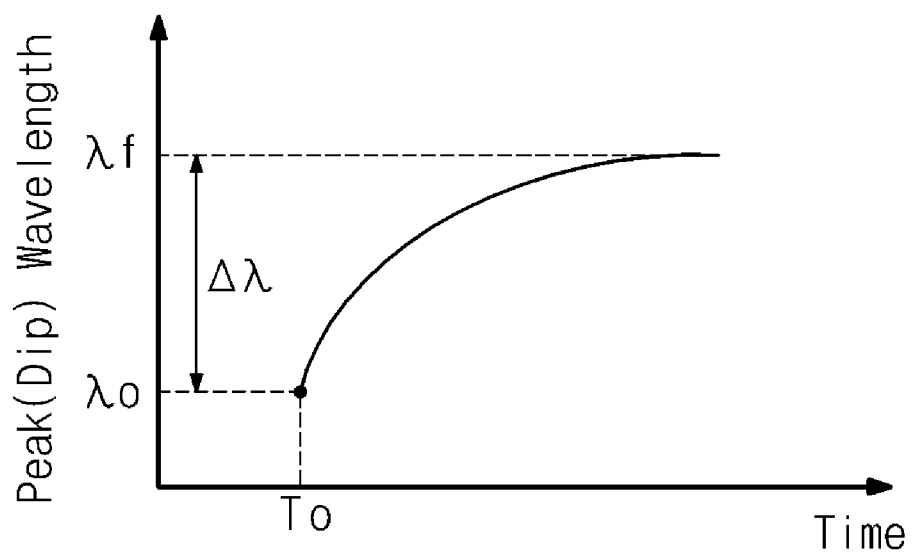
FIG. 2 is a graph illustrating a variation of a peak (or a dip) wavelength with time in a reflectance (or transmittance) spectrum.

FIG. 2 is a graph illustrating a variation of a peak (or a dip) wavelength with time in a reflectance (or transmittance) spectrum.

Referring to FIG. 2, when the sample contacts the biosensor at the time of $T_0$, a peak or a dip is generated in the reflectance (or transmittance) spectrum at the wavelength of $\lambda_0$. The variation of a wavelength is measured when the wavelength is not changed anymore at the maximum wavelength with time. Since the wavelength variation is determined by a concentration of the sample antigen, the concentration of the sample antigen may be obtained from the wavelength variation $\Delta\lambda$.

Figure 3:
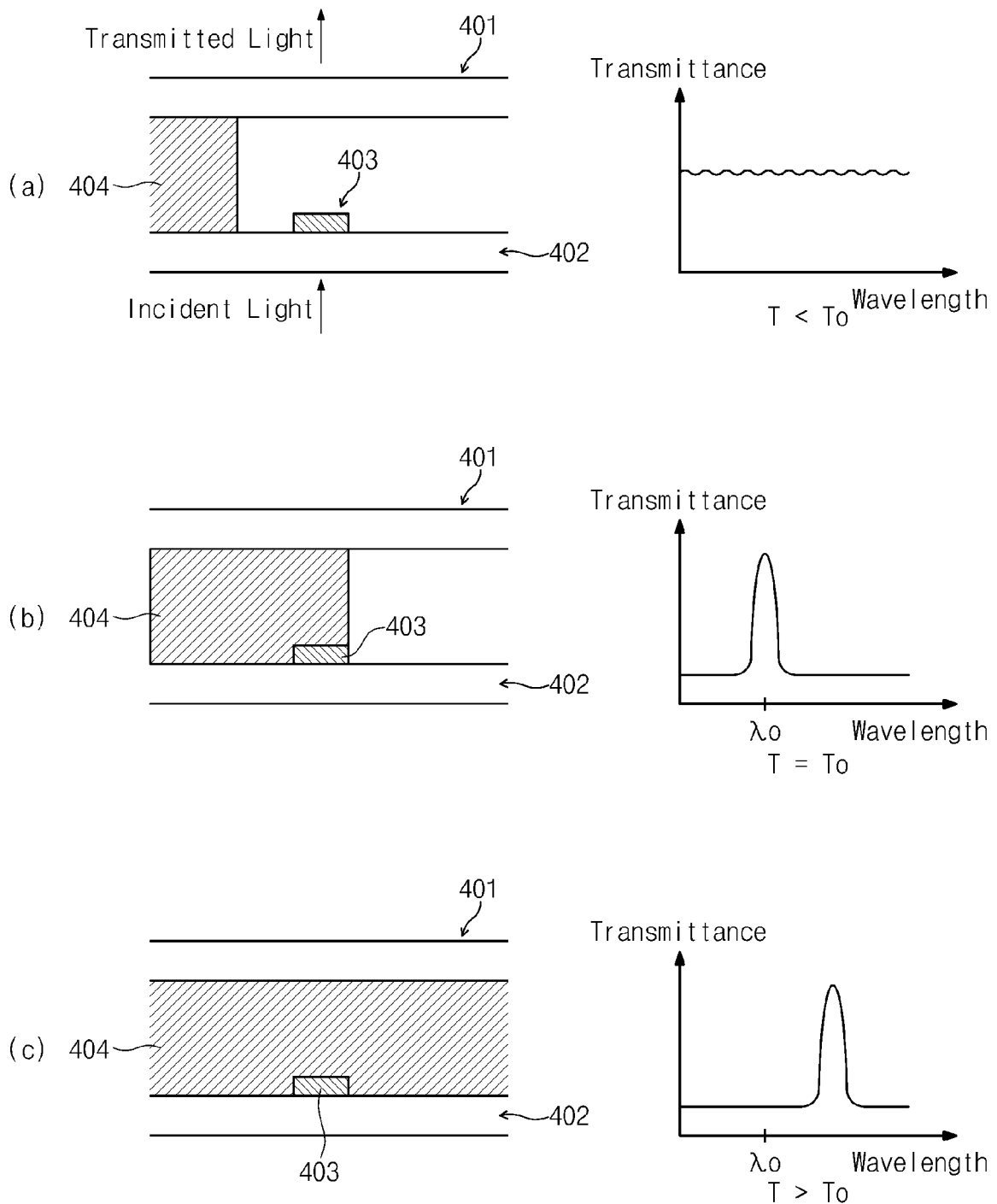
FIG. 3 is a diagram illustrating a peak formed in a transmittance spectrum when a sample contacts an antibody.

FIG. 3 is a diagram illustrating a peak formed in a transmittance spectrum when a sample contacts an antibody.

Referring to FIG. 3, a specific antibody 403 is fixed on a lower plate 402 of a biosensor chip. The lower plate 402 of the biosensor chip is covered with an upper plate 401 of the biosensor chip. The biosensor chip may include a channel to allow the sample 404 to flow into an antibody. The sample 404 includes an antigen reacting with the biosensor 103 where a specific antibody is fixed. The upper plate 401 and the lower plate 402 of the biosensor chip are transparent enough to transmit incident light.

As illustrated in FIGS. 1 and 2, a peak is generated in a reflectance spectrum when the sample reaches the antibody. As illustrated in FIG. 3(a) through 3(c), a peak may also be generated in a transmittance spectrum according to the type of the biosensor chip when the sample reaches the antibody. In this case, the concentration of the specific antigen can be measured by the variation of a dip wavelength.

Figure 4:
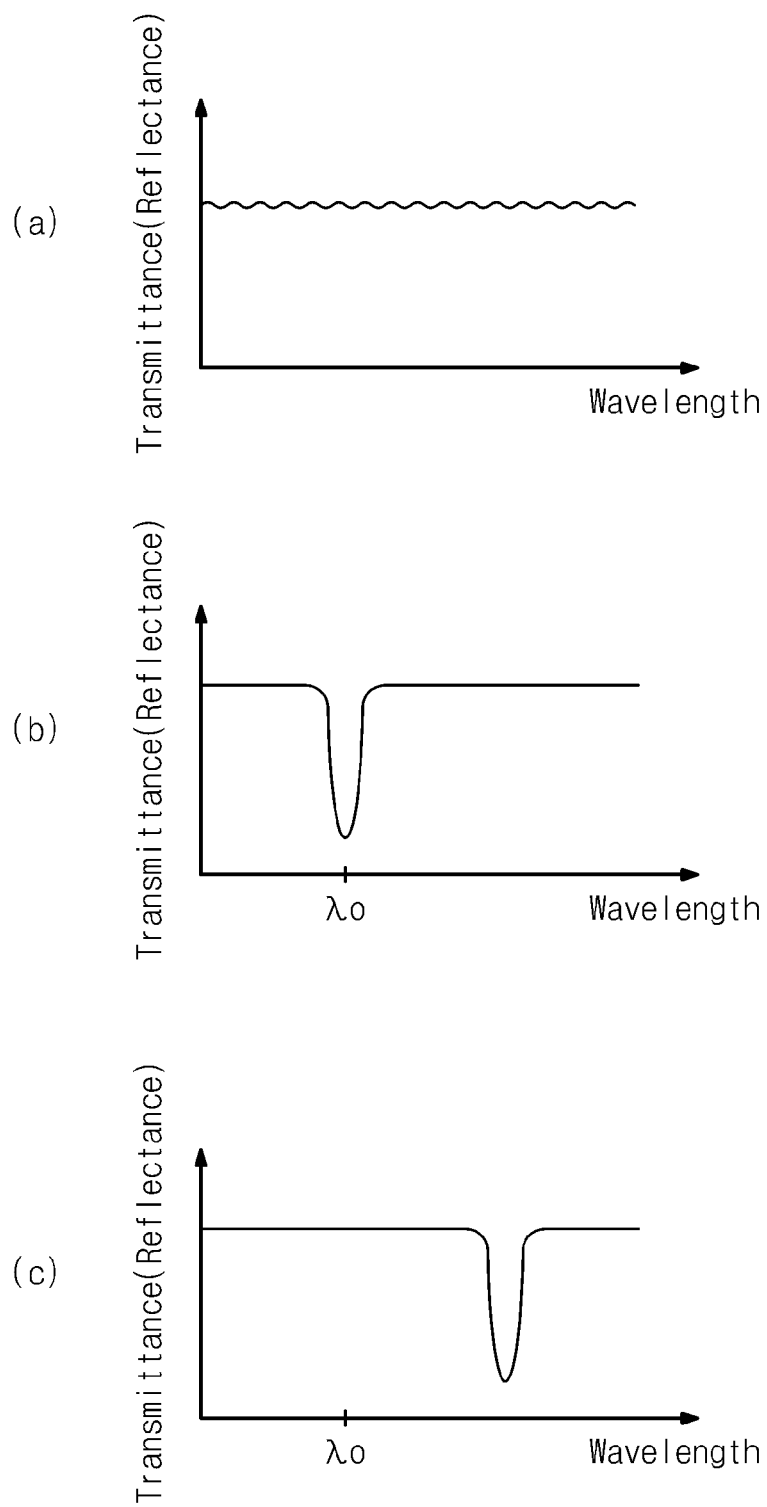
FIG. 4 is a diagram illustrating a dip generated in a transmittance or reflectance spectrum when a sample contacts an antibody.

FIG. 4 is a diagram illustrating a dip generated in a transmittance or reflectance spectrum when a sample contacts an antibody. Referring to FIG. 4, the concentration of the specific antigen can be measured by the variation of a dip wavelength.

Figure 5:
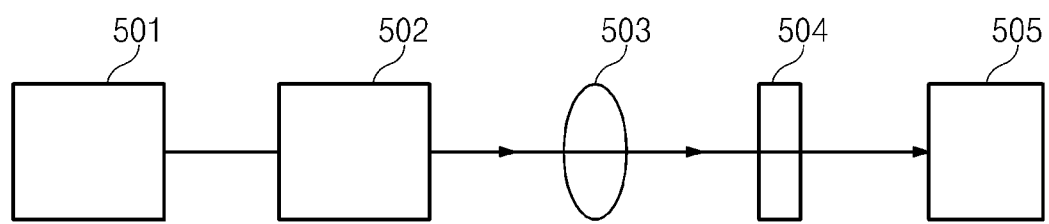
FIG. 5 is a diagram illustrating an optical biosensor measurement device for measuring transmittance according to an embodiment.

FIG. 5 is a diagram illustrating an optical biosensor measurement device for measuring transmittance according to an embodiment.

Referring to FIG. 5, the optical biosensor measurement device changes light emitted from a light source 502 having a wide line width into a parallel light by a lens 503. The parallel light is transmitted through an optical biosensor 504. The light from the optical biosensor 504 is measured using a spectroscope 505. The output of the light source is regulated by a light source regulator 501. A multi-channel measurement device such as a CCD camera or a single channel measurement device such as a Photo Diode (PD) and a Photo Multiplier Tube (PMT) is provided in the spectroscope 505. If the spectroscope includes a single channel measurement device, only one wavelength can be measured in one time. In this case, the wavelength must continually be changed in order to measure the spectrum.

Figure 6:
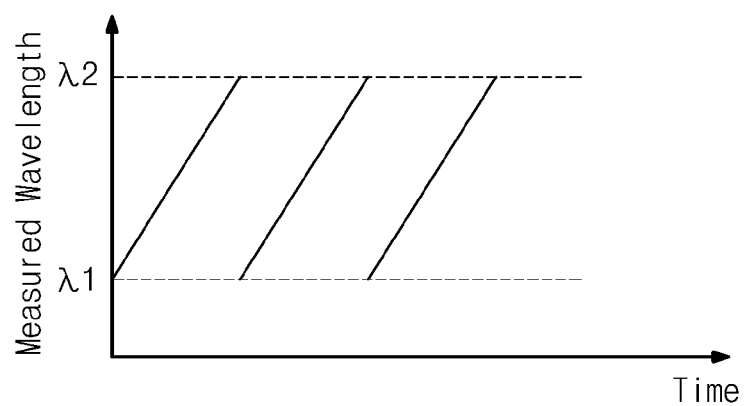
FIG. 6 is a graph illustrating a wavelength measurable by a spectroscope with the lapse of time.

FIG. 6 is a graph illustrating a wavelength measurable by a spectroscope with the lapse of time when a single channel measurement device is used. As illustrated in FIG. 6, a reflectance spectrum and a transmittance spectrum are repeatedly measured between measurement wavelengths $\lambda_1$ and $\lambda_2$.

Figure 7:
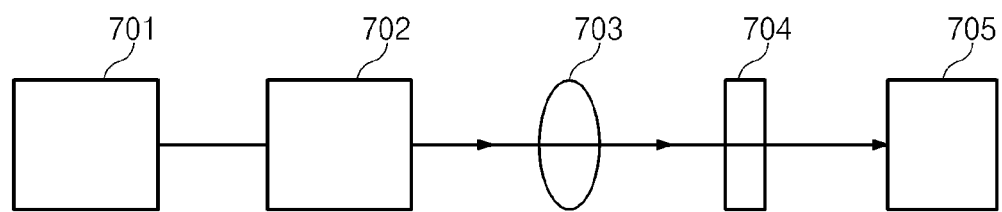
FIG. 7 is a diagram illustrating an optical characteristics measurement device for measuring transmittance using a wavelength-tunable light source and an optical power detector.

FIG. 7 is a diagram illustrating an optical characteristics measurement device for measuring transmittance using a wavelength-tunable light source and an optical power detector according to an embodiment.

Referring to FIG. 7, the optical characteristics measurement device regulates an optical power and an output wavelength of a wavelength-tunable light source 702 using a wavelength tunable regulator 701. The optical characteristics measurement device changes light emitted from the wavelength-tunable light source 702 into a parallel light using a lens 703, and measures light transmitted through a sample 704 by an optical power measurer 705. Since the optical characteristics measurement device can measure a reflectance of only one wavelength in one time, the wavelength must continually be changed in order to measure the spectrum. A graph illustrating a measurement wavelength with time of FIG. 7 is identical to the graph illustrated in FIG. 7.

Figure 8:
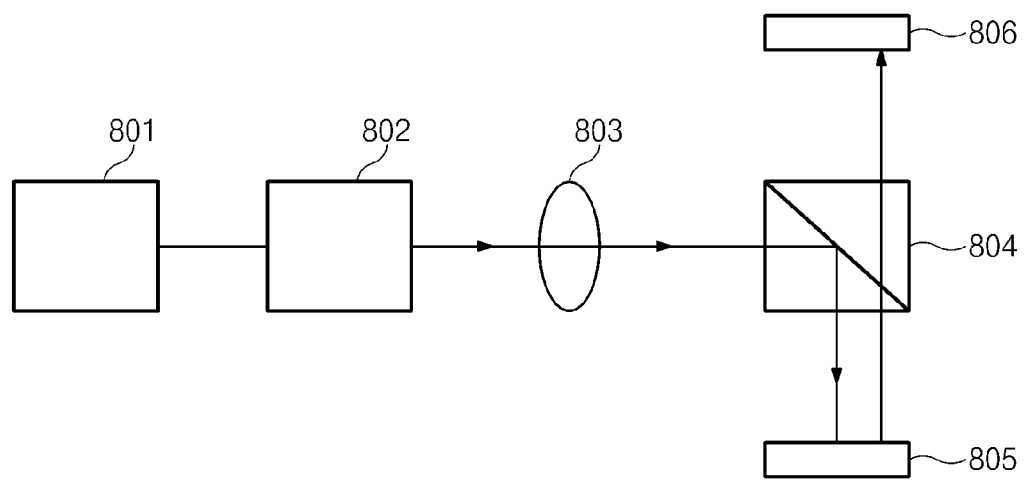
FIG. 8 is a diagram illustrating an optical biosensor optical characteristics measurement device for measuring reflectance according to an embodiment.

FIG. 8 is a diagram illustrating an optical biosensor optical characteristics measurement device for measuring reflectance according to an embodiment.

Referring to FIG. 8, the optical biosensor measurement device changes light emitted from a light source 802 having a wide line width into a parallel light using a lens 803. The light characteristics measurement device measures light reflected by a beam splitter 804 and a biosensor 805 using a spectroscope 806. The output of the light sources 802 is regulated using a light source regulator 801. A multi-channel measurement device such as a CCD camera or a single channel measurement device such as a Photo Diode (PD) and a Photo Multiplier Tube (PMT) may be provided in the spectroscope 806.

Figure 9:
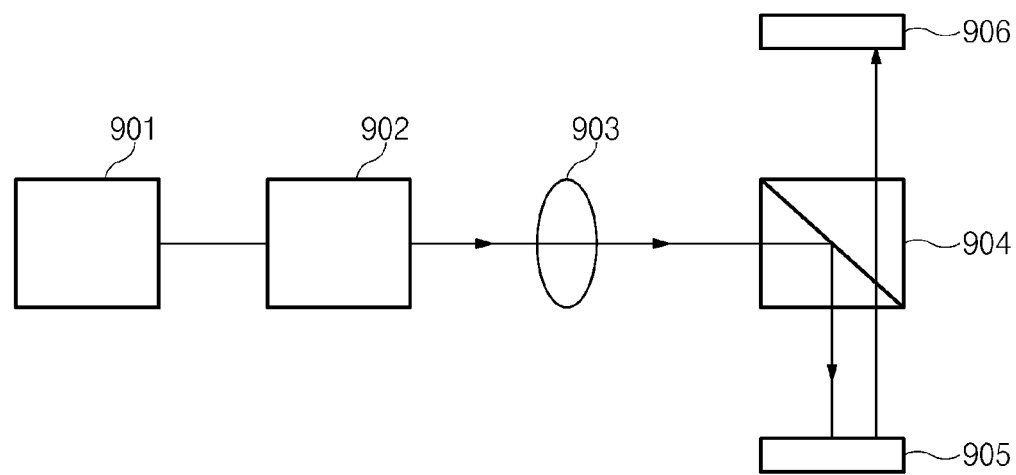
FIG. 9 is a diagram illustrating an optical characteristics measurement device for measuring reflectance using a wavelength-tunable light source and an optical power detector.

FIG. 9 is a diagram illustrating an optical characteristics measurement device for measuring reflectance using a wavelength-tunable light source and an optical power detector according to an embodiment.

Referring to FIG. 9, the optical characteristics measurement device controls a wavelength output of a wavelength-tunable light source 902 using a wavelength light source regulator 901. The optical characteristics measurement device changes light emitted from the wavelength-tunable light source 902 into a parallel light using a lens 903, and reflects the light to a biosensor 905 reacting with a sample using a beam splitter 904. The reflectance of the light reflected from the biosensor 905 is measured by an optical power measurer 906. The reflectance spectrum is measured by changing the wavelength of the wavelength-tunable light source 902 to measure a reflectance peak wavelength or a reflectance dip wavelength.

That is, the optical characteristics measurement device illustrated in FIG. 8 detects light using a spectroscope by reflecting a white light source to a biosensor. The optical characteristics measurement device detects light using an optical power measurer by reflecting a wavelength-tunable light source to a biosensor.

Figure 10:
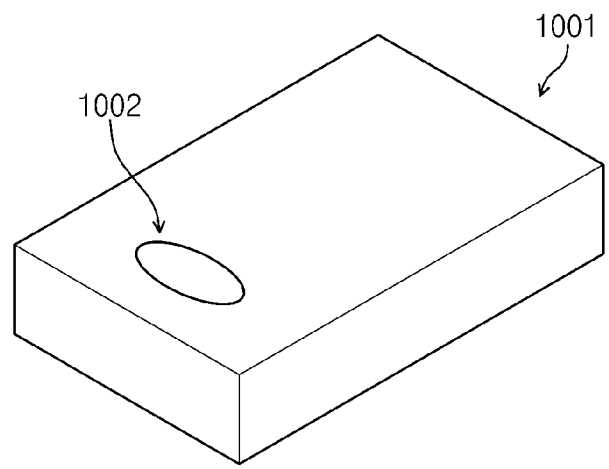
FIG. 10 is a diagram illustrating a biosensor chip according to an embodiment.

FIG. 10 is a diagram illustrating an actual biosensor chip according to an embodiment. As illustrated in FIG. 10, a biosensor chip 1001 includes a sample slot 1002.

Figure 11:
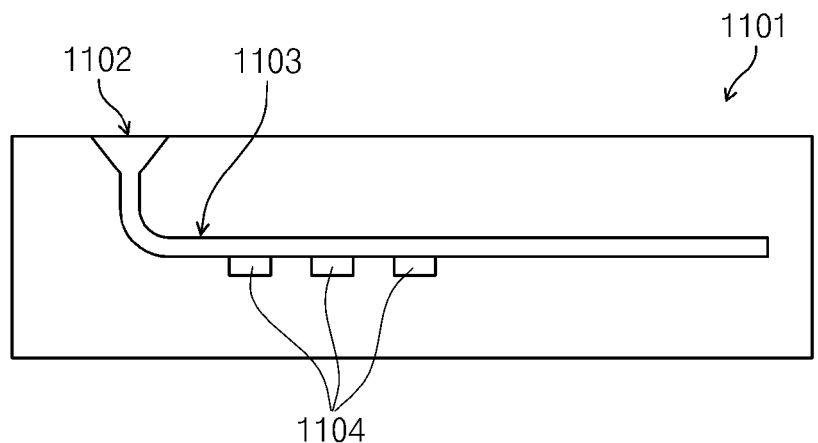
FIG. 11 is a diagram illustrating an internal structure of the typical biosensor chip of FIG. 10.

FIG. 11 is a diagram illustrating an internal structure of the typical biosensor chip of FIG. 10.

As illustrated in FIG. 11, a biosensor chip 1101 includes a channel 1103 allowing a sample to flow into a sample slot 1102. The biosensor chip 1101 includes one or more sensors 1104. A specific antigen is fixed on the sensor. The biosensor chip 1101 may be mounted in a measurement device before or after a sample is poured into the biosensor chip 1101.

As illustrated in FIG. 11, time is taken for the sample poured into the sample slot to reach an antibody. To obtain exact measurement results, the reflectance (or transmittance) spectrum is measured at the time when the sample contacts the antibody. Accordingly, as described in FIG. 2, a peak wavelength or a dip wavelength is measured to measure an exact wavelength variation $\Delta\lambda$ at the time when the sample contacts the antibody.

In the biosensor chip of FIG. 11, as described in the embodiments of FIGS. 5 and 8, a spectrum variation may be measured in real-time when a light source having a wide line width and a multi-channel measurement device are used. In this embodiment, the time point $T_0$ may be measured by a peak or a dip when the sample reaches the antibody. The biosensor chip may measure the transmittance or the reflectance of one wavelength in one time if a single channel measurement device such as PD and PMT as described in FIGS. 5 and 8, or a wavelength-tunable light source and an optical measurement device as described in FIGS. 7 and 9 are used. Also, since speeds of changing a measurement wavelength of a spectroscope and changing an output wavelength of the wavelength-tunable light source are limited, the time point $T_0$ when the sample reaches the antibody may not be measured.

Figure 12:
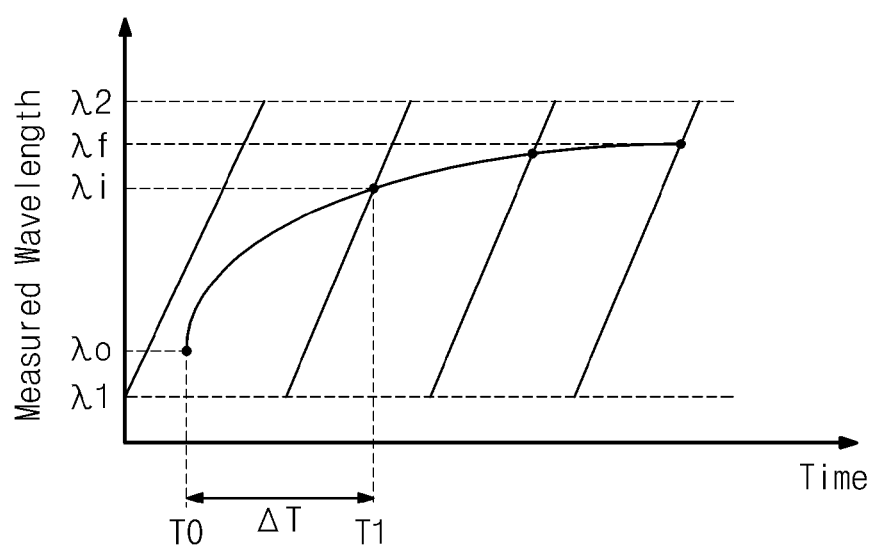
FIG. 12 is a graph illustrating a relation between a measurement wavelength with time and a peak wavelength (or dip wavelength) of actual transmittance (or reflectance)

FIG. 12 is a graph illustrating a relation between a measurement wavelength with time and a peak wavelength (or dip wavelength) of actual transmittance (or reflectance).

Referring to FIG. 12, a biosensor reader measures transmittance (or reflectance) between $\lambda_1$ and $\lambda_2$. A measurement wavelength according to an antigen-antibody immune reaction by a sample of a biosensor is increased to be saturated with time. The saturated measurement wavelength is $\lambda_f$, and the measurement wavelength when saturation begins is $\lambda_i$.

A sample reaches an antibody at the time of $T_0$. If the transmittance (or reflectance) of a different wavelength is measured at the time of $T_0$, a peak wavelength (or a dip wavelength) of the transmittance (or reflectance) is measured at T1 of the next period. In this case, an error that the initial value of the peak wavelength (or a dip wavelength) is measured as $\lambda_I$ instead of $\lambda_0$ may occur. Accordingly, a measurement error that a measurement result is $\Delta\lambda=\lambda_f-\lambda_I$ instead of $\Delta\lambda=\lambda_f-\lambda_0$ may occur.

The optical biosensor measurement device according to the embodiment includes an optical biosensor chip having optical characteristics such as transmittance and reflectance varied according to whether a sample exist or not, and an optical biosensor reader having a function of detecting whether the sample exists or not using an optical biosensor chip.

As described FIGS. 5 and 8, when measurement is performed at the time of the contact between the sample and the antibody, there is a method using a light source having a wide line width, a spectroscope, and a multi-channel measurement device. The transmittance (or reflectance) spectrum may be measured using the multi-channel measurement device in real-time.

As illustrated in FIG. 12, the relation between the measurement wavelength and the peak wavelength (or the dip wavelength) of the actual transmittance (or reflectance) may be determined by the transmittance (or reflectance) spectrum before and after the time when a sample contacts an antibody as described in FIGS. 1 through 3. Accordingly, $\lambda_0$ may be measured by determining in real-time whether a peak or a dip is formed in the spectrum.

Figure 13A:
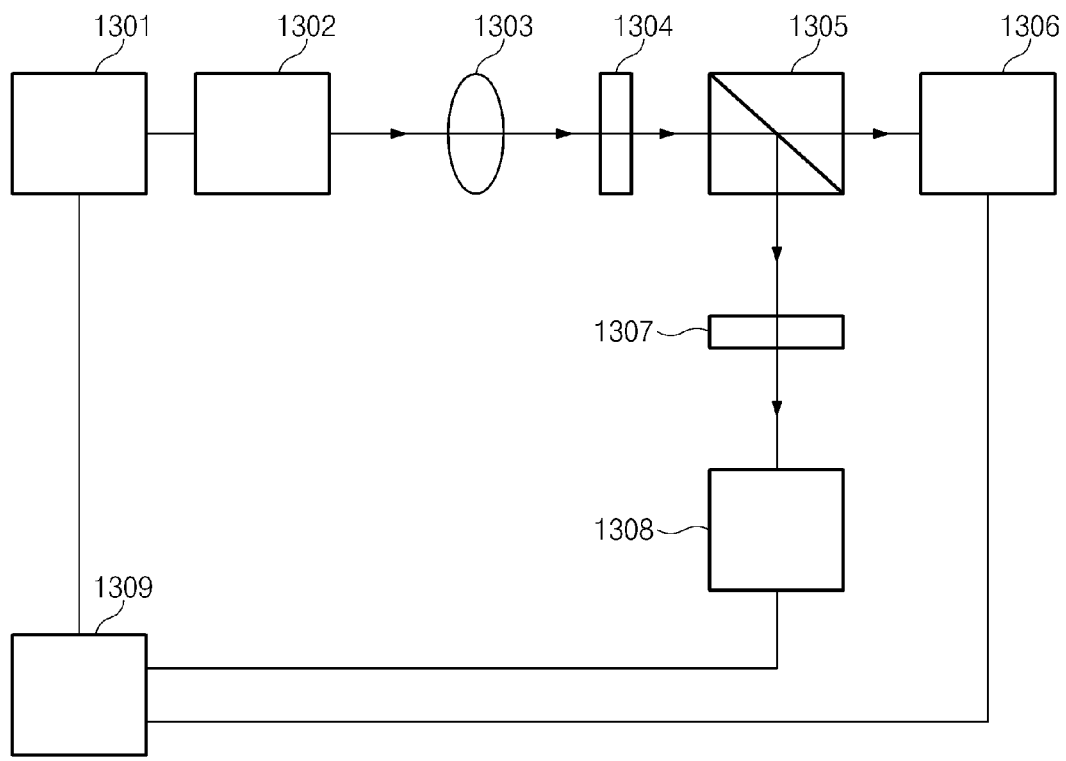
FIG. 13A is diagram illustrating the configuration of a measurement device detecting $T_0$ in a measurement device for measuring transmittance using a spectroscope and a single channel measurement device.

FIG. 13A is diagram illustrating the configuration of a measurement device detecting $T_0$ in a measurement device for measuring transmittance using a spectroscope and a single channel measurement device.

Referring to FIG. 13A, a measurement device according to an embodiment changes light emitted from a light source 1302 having a wide line width into a parallel light using a lens 1303. The measurement device divides light transmitted through a biosensor 1304 into two branches using a beam splitter 1305. One branched light is delivered to an optical power measurer 1308 through a spectroscope 1306, and the other branched light is delivered to the optical power measurer 1308 through an optical filter 1307. A single channel optical power measurer is provided in the spectroscope 1306. A light source regulator 1301 regulates the power of a light source 1302. A controller 1309 controls the measurement device.

As illustrated in FIG. 13A, the measurement device measures $T_0$ using an optical power detector such as a photo diode (PD) when transmittance is varied before and after contact of a sample and an antibody. Light reflected from a sensor is divided into two branches. One branched light is delivered to the spectroscope 1306, and the other branched light is delivered to the optical power measurer 1308. The reason why the optical filter 1307 is used is to increase a difference between optical power values measured by an optical measurement device 1308 before and after contact of the sample and the sensor.

FIGS. 13B through 13E are graphs illustrating a variation of the measurement device of FIG. 13A.

Figure 13B:
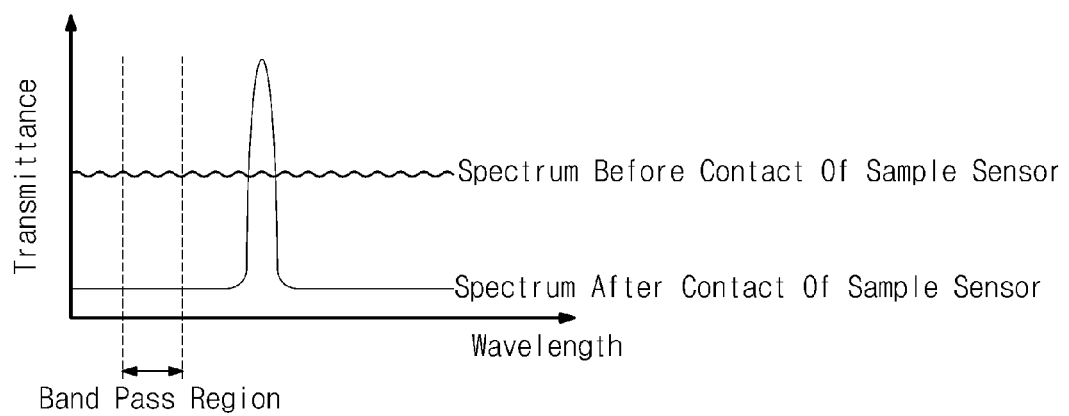
FIGS. 13B through 13E are graphs illustrating a variation of the measurement device of FIG. 13A.

Referring to FIGS. 13A and 13B, when a peak is generated in a transmittance spectrum after contact of a sample and a sensor, the measurement device measures the time of the contact of the sample and the sensor using a band pass filter. When an optical filter 1307 transmits only light of a band indicated in FIG. 13B, the difference between optical power values measured by an optical power measurer 1308 before and after the contact of the sample and the sensor is distinct, enabling detection of the time of contact between the sample and the sensor.

Figure 13C:
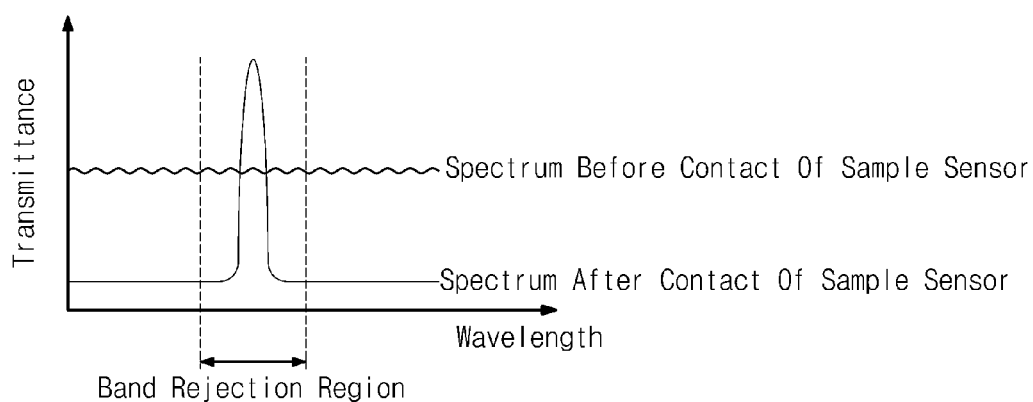

Referring to FIGS. 13A and 13C, when a peak is generated in the transmittance spectrum after the contact between the sample and the sensor, the measurement device measures the time of the contact of the sample and the sensor using a band rejection filter. Unless the optical filter 1307 transmits only light of a band indicated in FIG. 13C, the difference between optical power values measured by an optical power measurer 1308 before and after the contact of the sample and the sensor is distinct, enabling detection of the time of contact between the sample and the sensor.

Figure 13D:
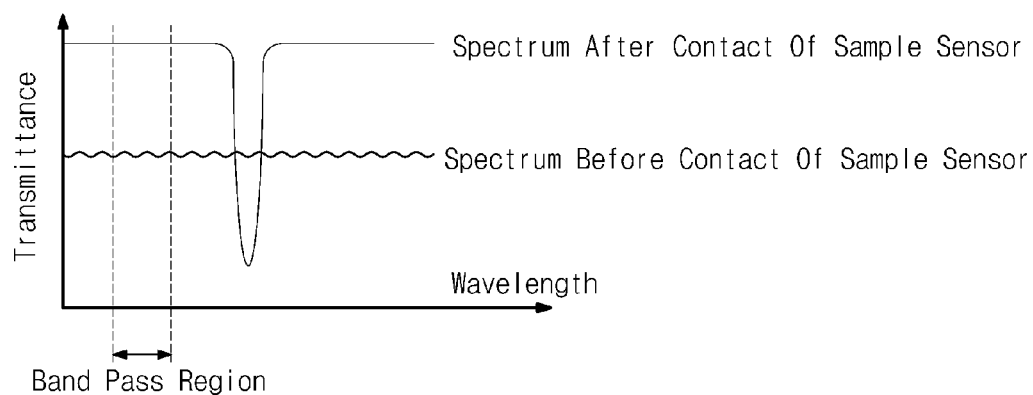

Referring to FIGS. 13A and 13D, when a dip is generated in a transmittance spectrum after contact of the sample and the sensor, the measurement device measures the time of the contact of the sample and the sensor using a band pass filter. When an optical filter 1307 transmits only light of a band indicated in FIG. 13D, the difference between optical power values measured by an optical power measurer 1308 before and after the contact of the sample and the sensor is distinct, enabling detection of the time of contact between the sample and the sensor.

Figure 13E:
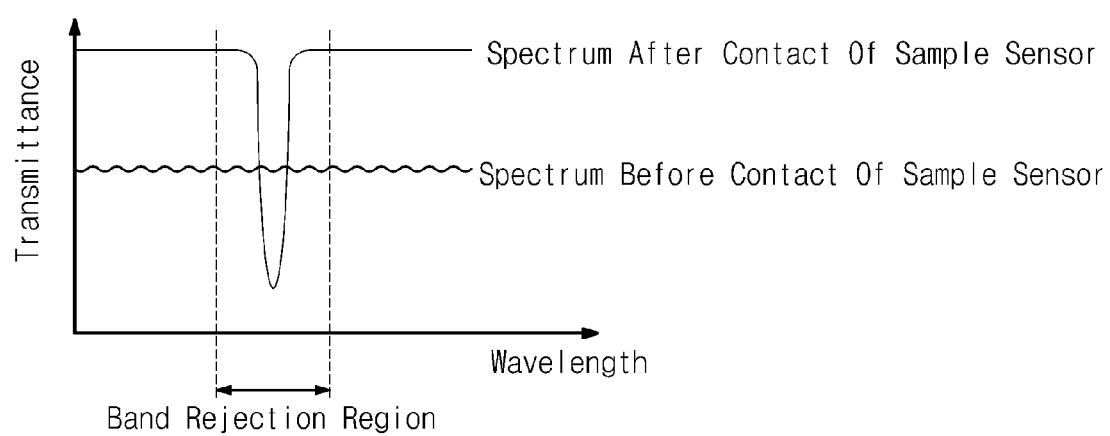

Referring to FIGS. 13A and 13E, when a dip is generated in the transmittance spectrum after the contact between the sample and the sensor, the measurement device measures the time of the contact between the sample and the sensor using a band rejection filter. Unless the optical filter 1307 transmits only light of a band indicated in FIG. 13E, the difference between optical power values measured by an optical power measurer 1308 before and after the contact of the sample and the sensor is distinct, enabling detection of the time of contact between the sample and the sensor.

The optical filter used in FIGS. 13A through 13E is not limited to any particular type, provided that it yields a distinct difference between the optical power values measured before and after contact between the sample and the sensor. In addition, the optical filter may be omitted if the difference between the optical power values measured before and after the contact between the sample and the sensor can easily be discriminated without the optical filter.

A variation of transmittance of a sensor is measured using a spectroscope after the time of the contact between the sample and the sensor is detected as described in FIGS. 13A through 13E.

Figure 14A:
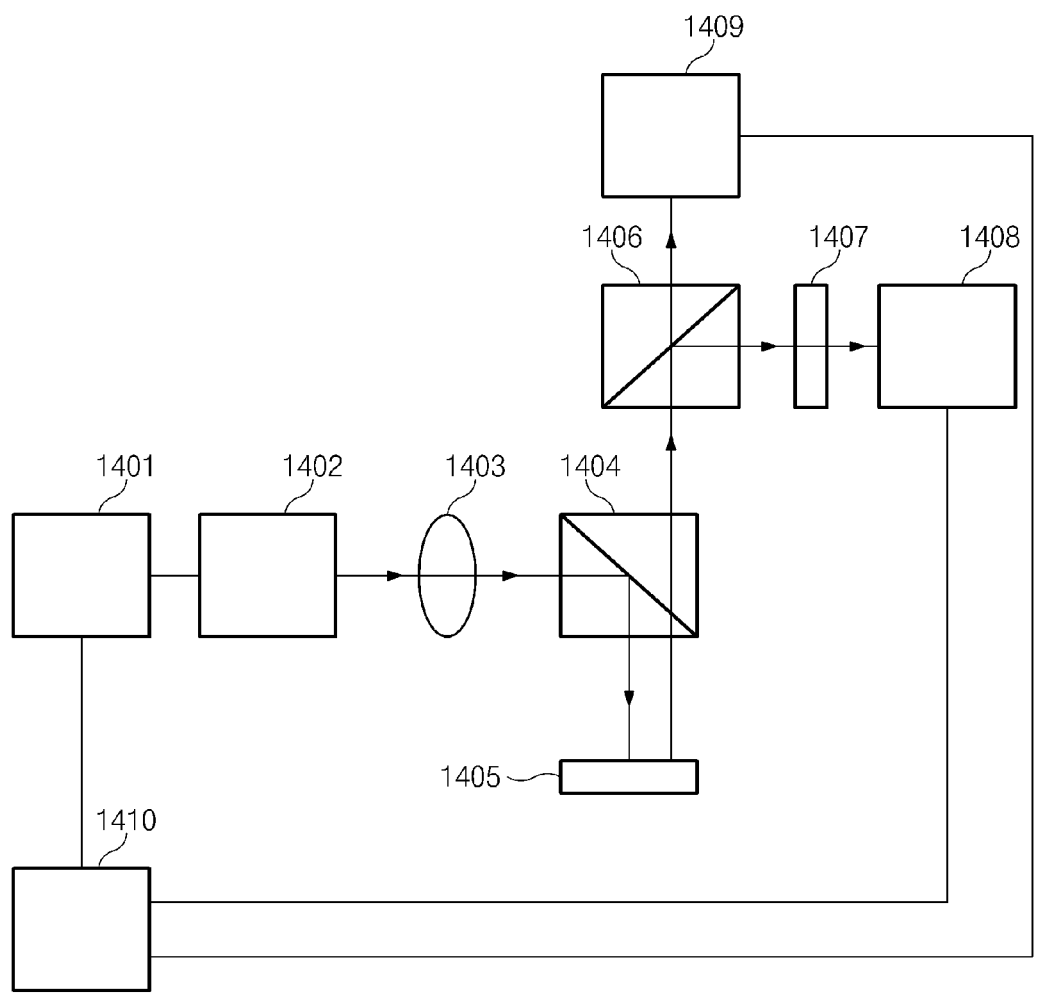
FIG. 14A is a diagram illustrating the configuration of a measurement device detecting $T_0$ in a measurement device for measuring reflectance using a spectroscope and a single channel measurement device.

FIG. 14A is a diagram illustrating the configuration of a measurement device detecting $T_0$ in a measurement device for measuring reflectance using a spectroscope and a single channel measurement device.

Referring to FIG. 14A, a measurement device according to an embodiment changes light emitted from a light source 1402 having a wide line width into a parallel light using a lens 1403. The measurement device divides light reflected by a first beam splitter 1404 and a biosensor 1405 into two branches using a second beam splitter 1406. One branched light is delivered to an optical power measurer 1408 through a spectroscope 1409, and the other branched light is delivered to the optical power measurer 1408 through an optical filter 1407. A single channel optical power measurer is provided in the spectroscope 1409. A light source regulator 1401 regulates the power of a light source 1402. A controller 1410 controls the measurement device. The measurement device measures $T_0$ using an optical power detector such as a photo diode (PD) when the output of the reflected light is varied before and after contact of a sample and an antibody. Light reflected from a sensor is divided into two branches. One branched light is delivered to the spectroscope 1409, and the other branched light is delivered to the optical power measurer 1408.

The reason why the measurement device of FIG. 14A uses the optical filter 1407 similar to that in FIG. 13A is to increase a difference between optical power values measured by an optical measurement device 1408 before and after contact of the sample and the sensor.

FIGS. 14B through 14E are graphs illustrating a variation of the measurement device of FIG. 14A.

Figure 14B:
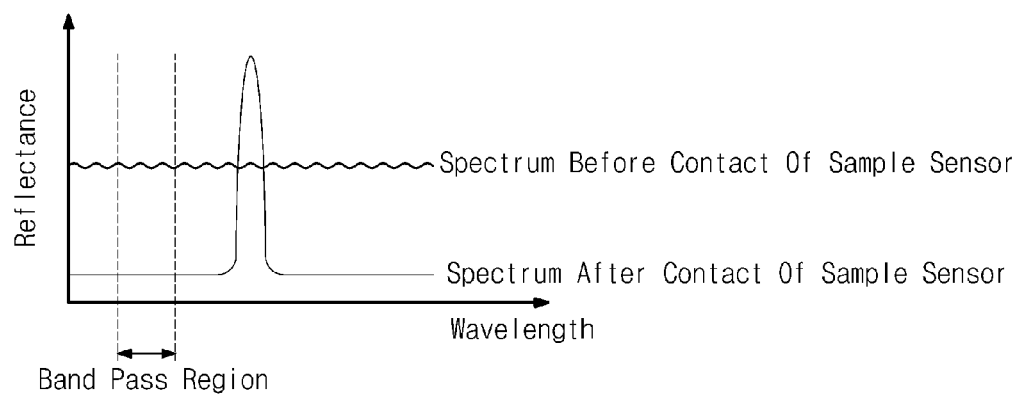
FIGS. 14B through 14E are graphs illustrating a variation of the measurement device of FIG. 14A.

Referring to FIGS. 14A and 14B, when a peak is generated in a transmittance spectrum after contact of a sample and a sensor, the measurement device measures the time of the contact of the sample and the sensor using a band pass filter. When an optical filter 1407 transmits only light of a band indicated in FIG. 14B, the difference between optical power values measured by an optical power measurer 1408 before and after the contact of the sample and the sensor is distinct, enabling detection of the time of contact between the sample and the sensor.

Figure 14C:
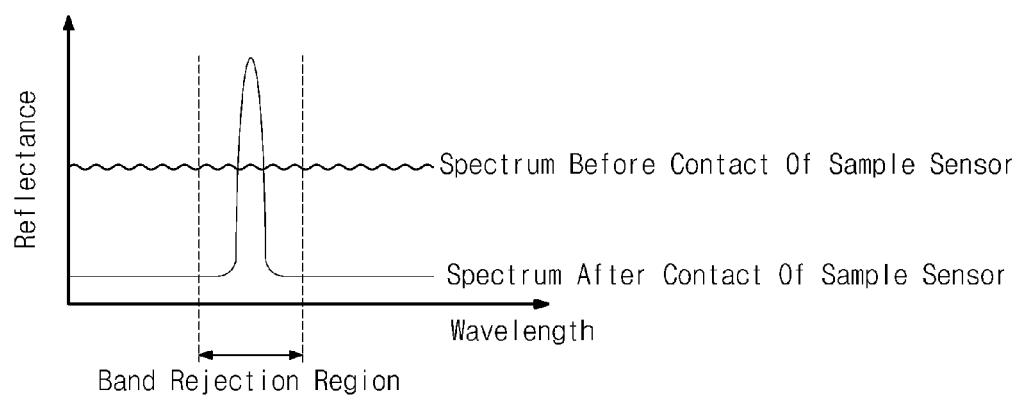

Referring to FIGS. 14A and 14C, when a peak is generated in the transmittance spectrum after the contact between the sample and the sensor, the measurement device measures the time of the contact between the sample and the sensor using a band rejection filter. Unless the optical filter 1407 transmits only light of a band indicated in FIG. 14C, the difference between optical power values measured by an optical power measurer 1408 before and after the contact of the sample and the sensor is distinct, enabling detection of the time of contact between the sample and the sensor.

Figure 14D:
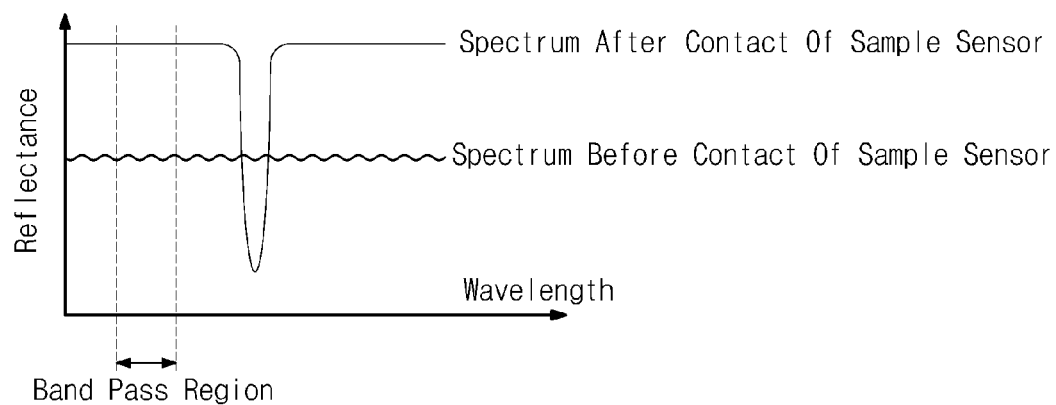

Referring to FIGS. 14A and 14D, when a dip is generated in a transmittance spectrum after contact of the sample and the sensor, the measurement device measures the time of the contact of the sample and the sensor using a band pass filter. When an optical filter 1407 transmits only light of a band indicated in FIG. 14D, the difference between optical power values measured by an optical power measurer 1408 before and after the contact of the sample and the sensor is distinct, enabling detection of the time of contact between the sample and the sensor.

Figure 14E:
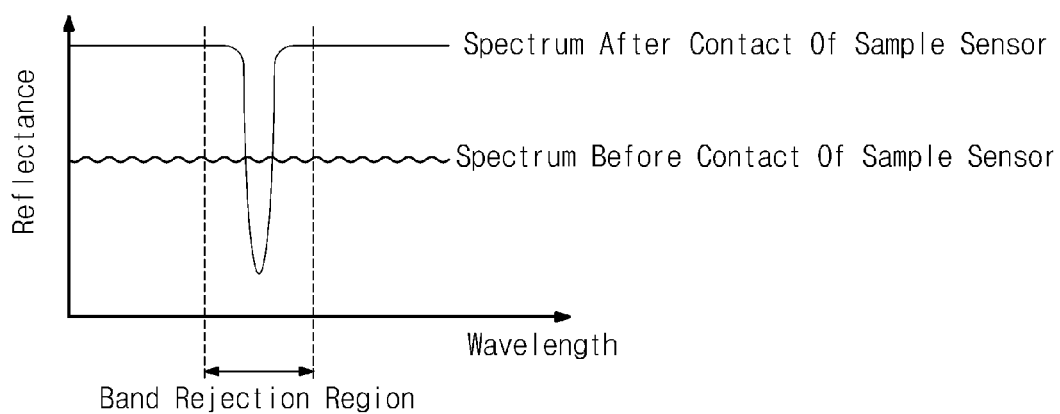

Referring to FIGS. 14A and 14E, when a dip is generated in the transmittance spectrum after the contact between the sample and the sensor, the measurement device measures the time of the contact between the sample and the sensor using a band rejection filter. Unless the optical filter 1407 transmits only light of a band indicated in FIG. 14E, the difference between optical power values measured by an optical power measurer 1408 before and after the contact of the sample and the sensor is distinct, enabling detection of the time of contact between the sample and the sensor.

The optical filter used in FIGS. 13A through 13E is not limited to any particular type, provided that it yields a distinct difference between the optical power values measured before and after the contact between the sample and the sensor. In addition, the optical filter may be omitted if the difference between the optical power values measured before and after the contact between the sample and the sensor can easily be discriminated without the optical filter.

A variation of transmittance of a sensor is measured using a spectroscope after the time of the contact between the sample and the sensor is detected as described in FIGS. 14A through 14E.

Figure 15A:
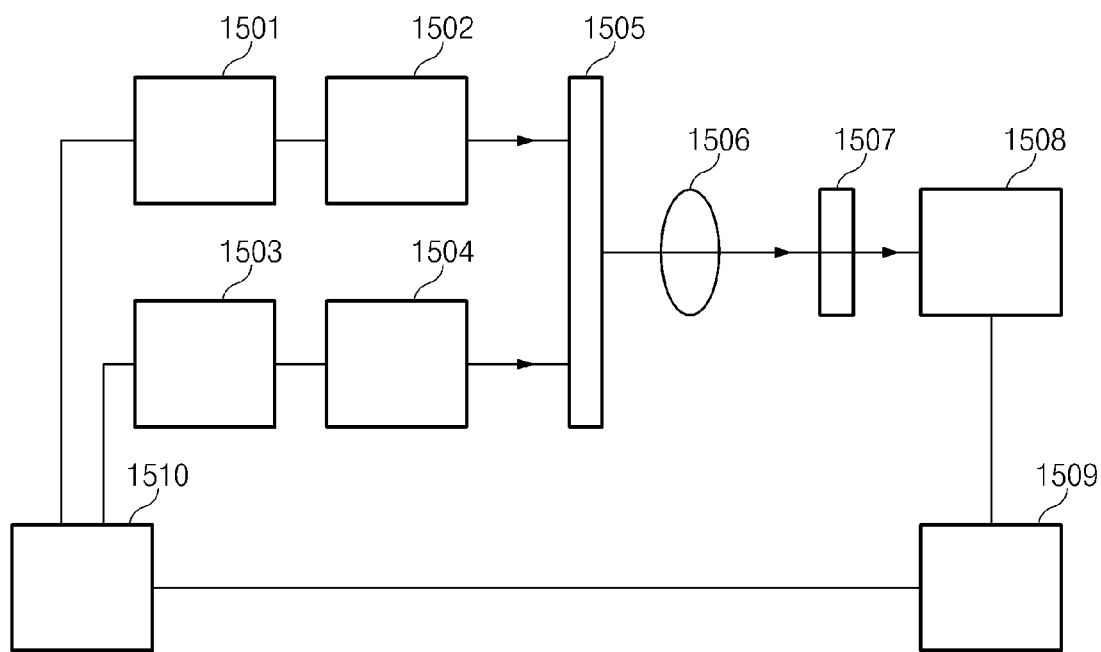
FIG. 15A is a diagram illustrating an example of measuring $T_0$ by installing an additional light source in an optical biosensor reader for measuring transmittance using a wavelength-tunable light source and an optical power measurer.

FIG. 15A is a diagram illustrating an example of measuring $T_0$ by installing an additional light source in an optical biosensor reader for measuring transmittance using a wavelength-tunable light source and an optical power measurer.

Referring to FIG. 15A, the measurement device regulates a wavelength output of a wavelength-tunable light source 1502 using a wavelength regulator 1501. The additional light source 1504 is not a wavelength-tunable light source but a wavelength-fixed light source. The output power of the additional light source 1504 is regulated by an additional light source regulator 1503. Light emitted from the wavelength-tunable light source 1502 and light emitted from the additional light source 1504 are united into one by a coupler 1505, which is changed into a parallel light by a lens 1506. Light transmitted through the biosensor 1507 is measured by an optical power measurer 1508. The measured signal is processed by a signal processing unit 1509. A controller 1510 controls the measurement device overall.

Figure 15B:
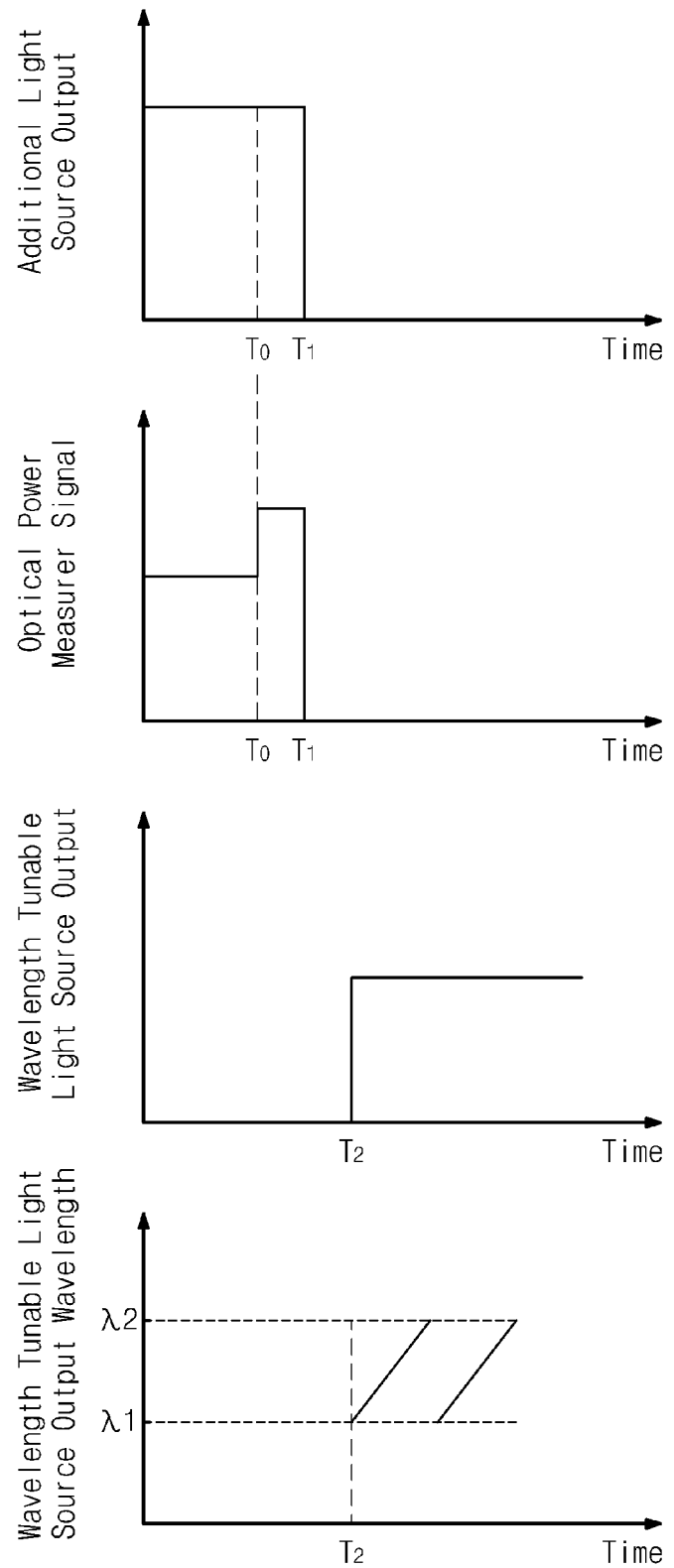
FIG. 15B is a diagram illustrating an example of measuring a variation of a transmittance spectrum using a wave tunable light source in the off-state of an additional light source after measuring a point T0 only using the additional light source in the off-state of the wavelength-tunable light source in FIG. 15A.

FIG. 15B is a diagram illustrating an example of measuring a variation of a transmittance spectrum using a wave tunable light source in the off-state of an additional light source after measuring point $T_0$ only using the additional light source in the off-state of the wavelength-tunable light source in FIG. 15A.

Referring to FIGS. 15A and 15B, the optical power measurer 1508 measures a variation of a signal (i.e., point $T_0$) using a reaction of the biosensor 1507. The signal processing unit 1509 processes a measured signal of the optical power measurer 1508 and transmits the signal to the controller 1510. The controller 1510 turns off the output power of the additional light source 1504 by controlling the additional light source regulator 1503 at T1.

The controller 1510 activates the wavelength-tunable light source 1502 by controlling the wavelength light source regulator 1501. The wavelength light source regulator 1501 gradually increases an output wavelength from $\lambda_1$ to $\lambda_2$ repeatedly. The optical power measurer 1508 measures a variation of a transmittance spectrum using light transmitted through the biosensor 1507.

A time interval between $T_0$ and $T_2$ is determined by the wavelength-tunable light source regulator 1501, the wavelength-tunable light source 1502, the additional light source regulator 1503, the additional light source 1504, the optical power measurer 1508, the signal processing unit 1509, and the controller 1510. The time interval may be less than several tens of milliseconds.

Figure 15C:
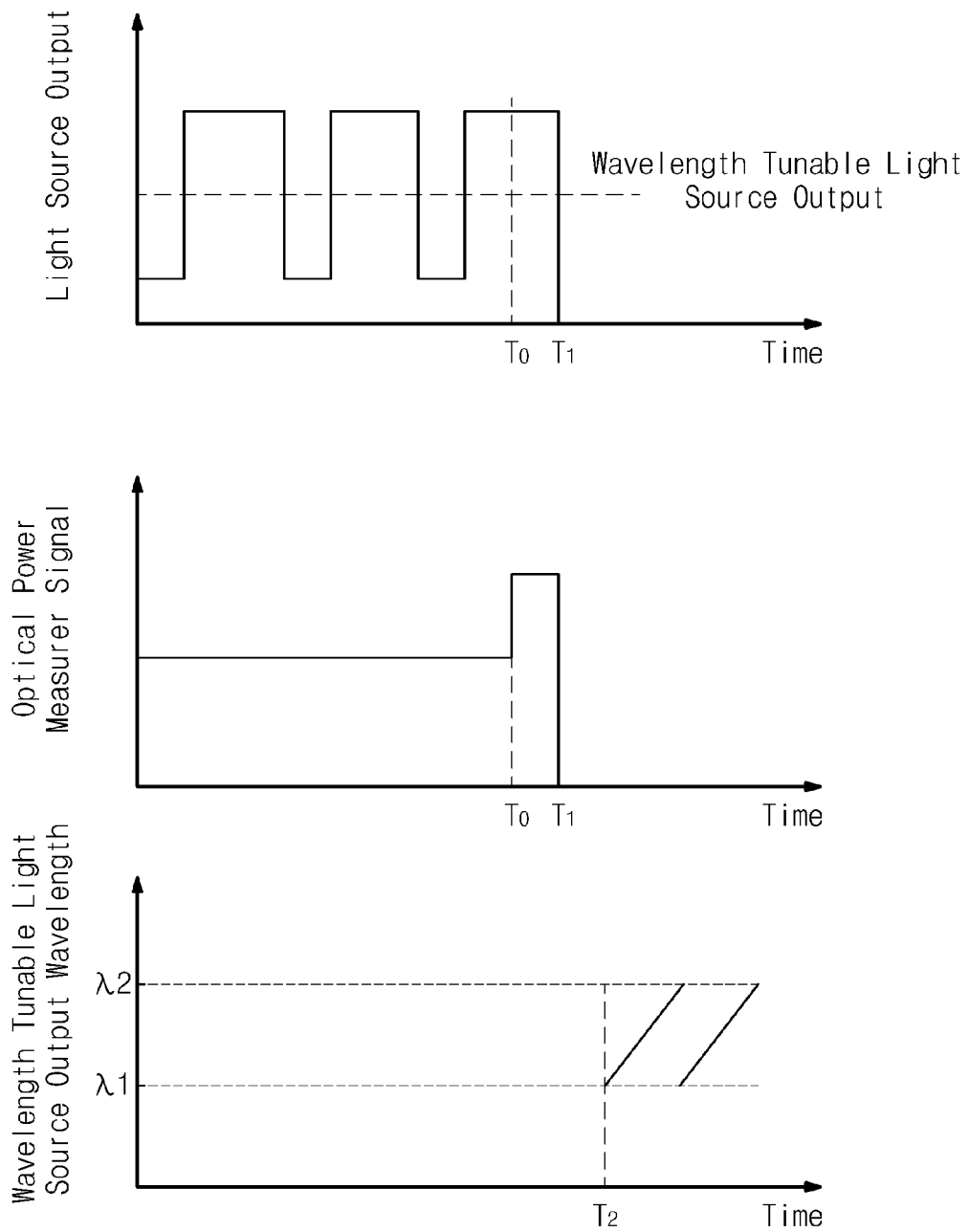
FIG. 15C is a diagram illustrating an example of measuring a time point by maintaining an output of a wavelength-tunable light source constant and modulating an output of an additional light source into a square wave or a sine wave in FIG. 15A.

FIG. 15C is a diagram illustrating an example of measuring a time point by maintaining an output of a wavelength-tunable light source constant and modulating an output of an additional light source into a square wave or a sine wave in FIG. 15A.

Referring to FIG. 15C, the signal processing unit 1509 may separate one signal transmitted from the optical power measurer 1508 into a signal by the wavelength-tunable light source 1502 and a signal by the additional light source 1504. The output of the light source irradiated from the additional light source 1504 is varied with time. The output of the light source irradiated from the wavelength-tunable light source 1502 is constant with time. The additional light source 1504 is added to search for the exact initial reaction point of the sample. The signal processing unit 1509 measures the variation of the separated signal magnitude by the additional light source to confirm the time point $T_0$ (i.e., the initial reaction point of the sample). The signal processing unit 1509 processes the measured signal of the optical power measurer 1508 to transmit to the controller 1510. The controller 1510 turns off the output power of the additional light source 1504 by controlling the additional light source regulator 1503 at the time point T1. Then, at the time point T2, the wavelength-tunable light source 1502 outputs a wavelength from $\lambda_1$ to $\lambda_2$ repeatedly in response to the control of the wavelength light source regulator 1501 until $\lambda_f$ (that is, when a measurement wavelength is saturated according to an antigen-antibody immune reaction) as described in FIG. 12 is obtained. A time interval between $T_0$ and $T_2$ is determined by the wavelength-tunable light source regulator 1501, the wavelength-tunable light source 1502, the additional light source regulator 1503, the additional light source 1504, the optical power measurer

1508, the signal processing unit 1509, and the controller 1510. The time interval may be less than several tens of milliseconds.

The output wavelength of $T_0$ light source may be applied without limitation if there is a distinct difference between reflectances (or transmittances) before and after contact between the sample and the sensor. The wavelength region of the $T_0$ light source may be within or beyond a range from $\lambda_1$ to $\lambda_2$.

Figure 16:
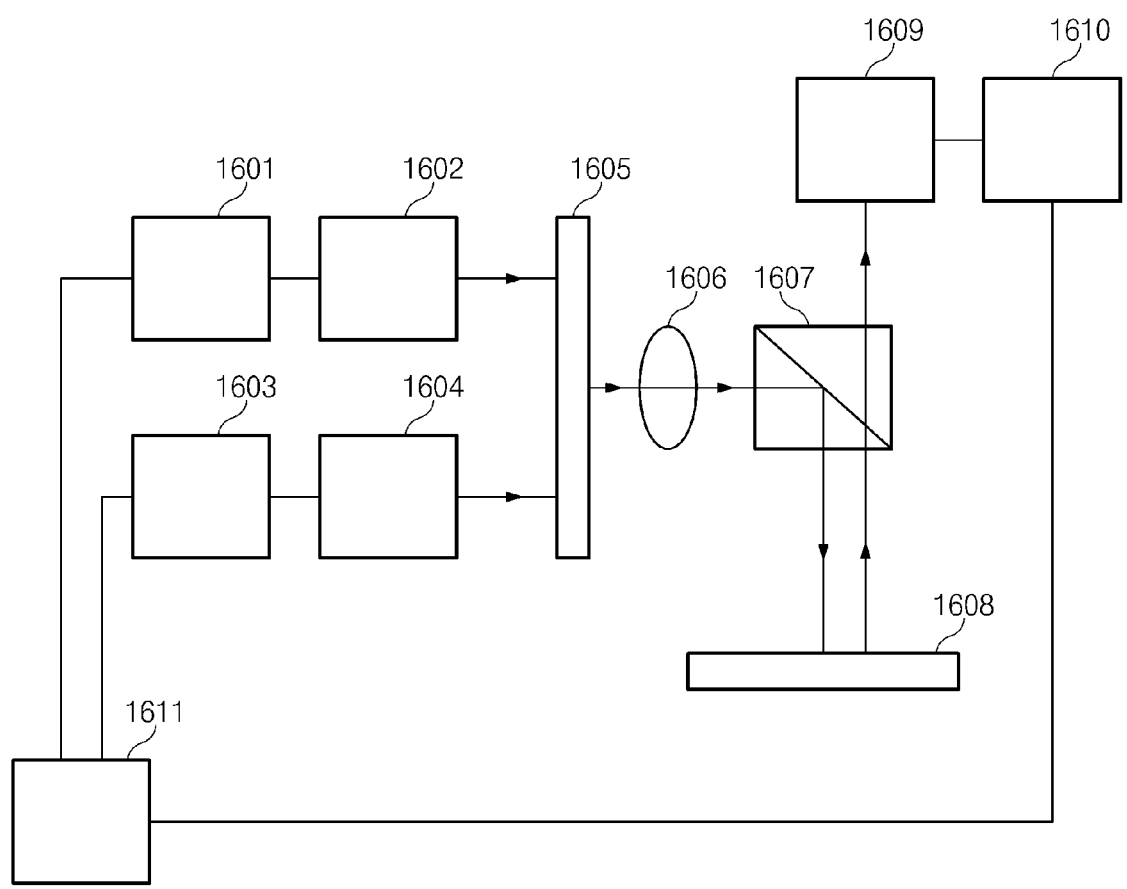
FIG. 16 is a diagram illustrating an example of measuring $T_0$ by installing an additional light source in an optical biosensor reader for measuring reflectance using a wavelength-tunable light source and an optical power measurer.

FIG. 16 is a diagram illustrating an example of measuring $T_0$ by installing an additional light source in an optical biosensor reader for measuring reflectance using a wavelength-tunable light source and an optical power measurer.

While a transmittance spectrum is used in FIG. 15A, a reflectance spectrum is used in FIG. 16. Therefore, the graphs in FIGS. 15B and 15C will be applied to FIG. 16.

Referring to FIG. 16, a measurement device regulates an optical power and an output wavelength of a wavelength-tunable light source 1602 using a wavelength light source regulator 1601. An additional light source 1604 is not a wavelength-tunable light source but a wavelength-fixed light source. The output of the additional light source 1604 is regulated using an additional light source regulator 1603.

Light emitted from the wavelength-tunable light source 1602 and light emitted from the additional light source 1604 are united into one by a coupler 1605, which is changed into a parallel light by a lens 1606. Light reflected by a beam splitter 1607 and a biosensor 1608 is measured by an optical power measurer 1608. The measured signal is processed by a signal processing unit 1610. A controller 1611 controls the measurement device overall.

Figure 17B:
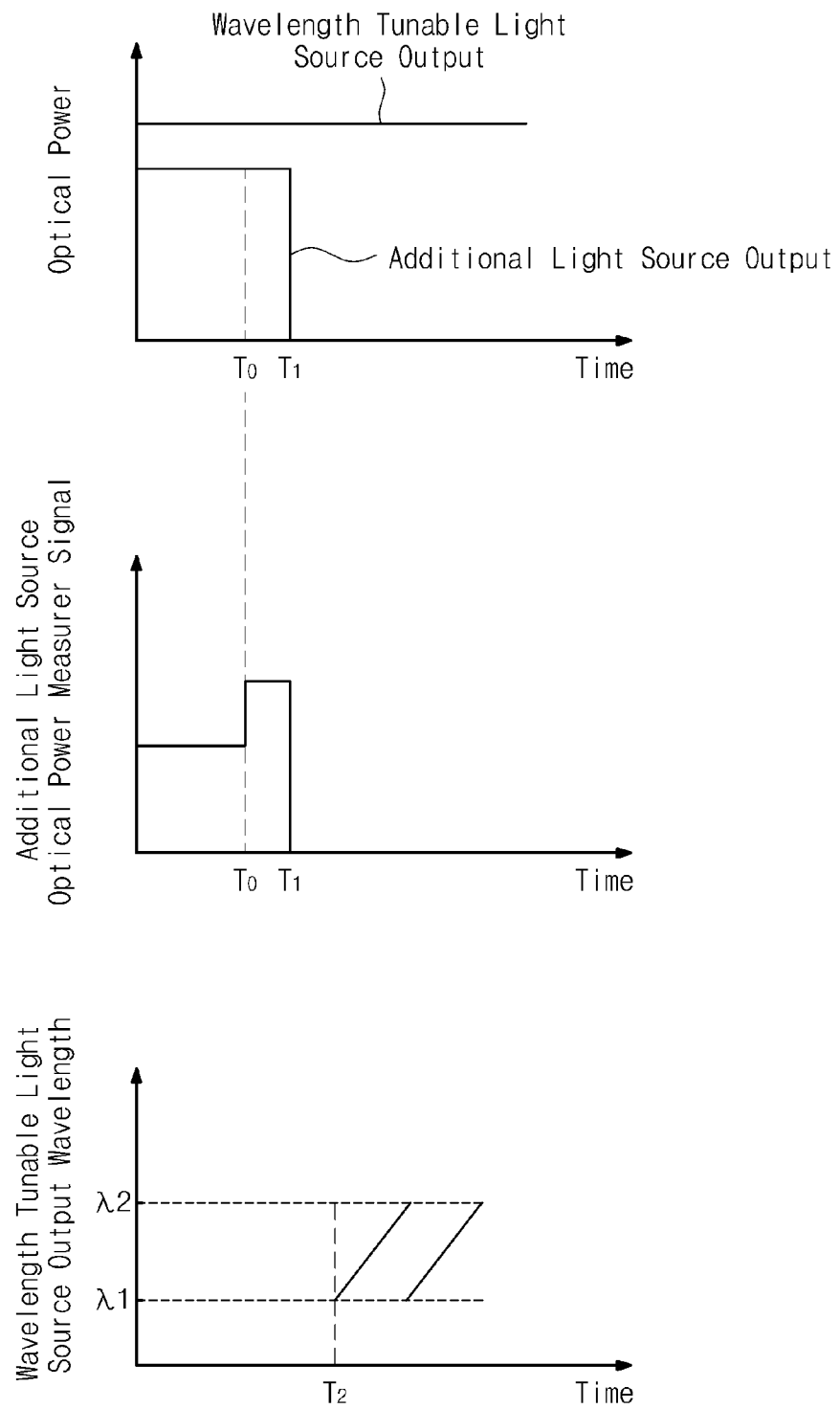
FIG. 17B is a diagram illustrating an example of measuring a variation of a transmittance spectrum using a wave tunable light source in the off-state of an additional light source after measuring a point $T_0$ only using the additional light source in the off-state of the wavelength-tunable light source in FIG. 17A.

FIG. 17A is a diagram illustrating an optical biosensor measurement device according to a second embodiment. A method of separating light transmitted through a biosensor using an optical filter is described in FIGS. 17A and 17B. Without modulating an additional light source as described in FIG. 15, the method considers that output wavelengths of a wavelength-tunable light source and an additional light source are different.

Referring to FIG. 17A, the measurement device regulates the optical power and the output wavelength of a wavelength-tunable light source 1702 using a wavelength light source regulator 1701 in response to the control of a controller 1712. A light source regulator 1703 controls an additional light source 1704 to drive in response to the control of the controller 1712. The additional light source 1704 is not wavelength-tunable light but wavelength-fixed light.

Light emitted from the wavelength-tunable light source 1702 and light emitted from the additional light source 1704 are united into one. The light outputted from the coupler 1705 is changed into a parallel light by a lens 1706.

The measurement device separates the light from the wavelength-tunable light source 1702 and the light from the additional light source 1704 using an optical component 1708 having transmittance and reflectance varied with wavelength, and delivers the separated lights to an optical power measurer 1709 of the wavelength-tunable light source 1702 and an optical power measurer 1710 of the additional light source 1704, respectively.

The optical component 1708 has transmittance and reflectance varied with wavelength. The optical component 1708 separates the light from the wavelength-tunable light source 1702 and the light from the additional light source 1704 using an optical component 1708 having transmittance and reflectance varied with wavelength, and delivers the separated lights to an optical power measurer 1709 of the wavelength-tunable light source 1702 and an optical power measurer 1710 of the additional light source 1704, respectively.

A signal processing unit 1711 detects time point $T_0$ when the optical power measured by the additional light source optical power measurement device 1710 in response to the control of the controller 1712 is changed by a predetermined value or more. At the detected time point, a sample contacts a sensor.

FIG. 17B is a diagram illustrating an example of measuring a variation of a transmittance spectrum using a wave tunable light source in the off-state of an additional light source after measuring a point $T_0$ only using the additional light source in the off-state of the wavelength-tunable light source in FIG. 17A.

Referring to FIGS. 17A and 17B, the additional light source optical power measurer 1710 measures a variation of a signal (i.e., T0 time point) using a reaction of the biosensor 1707. The signal processing unit 1711 processes a measured signal of the additional light source optical power measurer 1710 and transmits the signal to the controller 1712. The controller 1712 turns off the output power of the additional light source 1704 by controlling the additional light source regulator 1703 at the time point T1.

The controller 1712 activates the wavelength-tunable light source 1702 by controlling the wavelength light source regulator 1701 at the time point T2. The wavelength light source regulator 1701 gradually increases an output wavelength from $\lambda_1$ to $\lambda_2$ repeatedly. The optical power measurer 1709 measures a variation of a transmittance spectrum using light transmitted through the biosensor 1707. Then, at the time point T2, the wavelength-tunable light source 1702 outputs a wavelength from $\lambda_1$ to $\lambda_2$ repeatedly in response to the control of the wavelength light source regulator 1701 until $\lambda_f$ (that is, when a measurement wavelength is saturated according to an antigen-antibody immune reaction) as described in FIG. 12 is obtained. The optical power measurer 1709 measures a biosensor 1707 using only the wavelength light source 1702.

Figure 18:
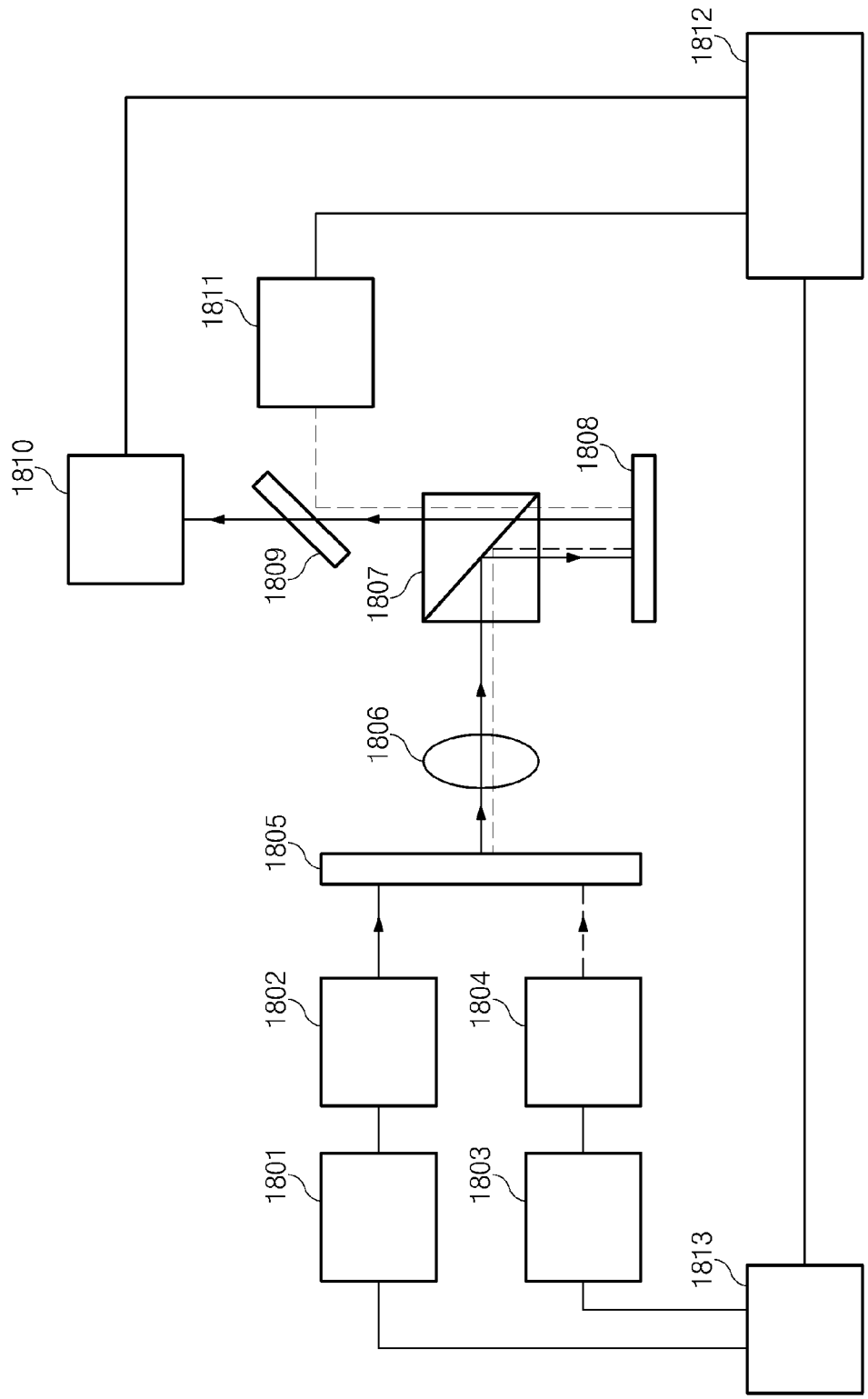
FIG. 18 is a diagram illustrating an optical biosensor measurement device according to a third embodiment.

FIG. 18 illustrates a method of separating light transmitted through a biosensor using an optical filter. Without modulating an additional light source, the method considers that output wavelengths of a wavelength-tunable light source and the additional light source are different.

Referring to FIG. 18, the measurement device regulates the optical power and the output wavelength of a wavelength-tunable light source 1802 using a wavelength light source regulator 1801 in response to the control of a controller 1813. The light source regulator 1803 controls an additional light source 1804 to drive in response to the control of the controller 1813. The additional light source 1804 is not a wavelength-tunable light but a wavelength-fixed light.

Light emitted from the wavelength-tunable light source 1802 and light emitted from the additional light source 1804 are united into one by a coupler 1805. The light outputted from the coupler 1805 is changed into a parallel light by a lens 1806 to be projected to a beam splitter 1807.

The light reflected the beam splitter 1807 and a biosensor 1808 is projected to an optical component 1809. The optical component 1809 has transmittance and reflectance varied with wavelength. The optical component 1809 separates the light from the wavelength-tunable light source 1802 and the light from the additional light source 1804, and transmits the separated lights to the wavelength-tunable light source optical power measurer 1810 and the additional light source optical power measurer 1811, respectively.

Referring again to FIG. 18, the additional light source optical power measurer 1811 measures a variation (i.e., time point T0) of a signal using a reaction of the biosensor 1808. A signal processing unit 1812 processes the measured signal of the additional light source optical power measurer 1811 to transmit the controller 1813. The controller 1813 turns off the output power of the additional light source 1804 by controlling the additional light source regulator 1803 at the time point T1.

The controller 1813 activates the wavelength-tunable light source 1802 by controlling the wavelength light source regulator 1801 at the time point T2. The wavelength light source regulator 1801 gradually increases an output wavelength from $\lambda_1$ to $\lambda_2$ repeatedly. The optical power measurer 1810 measures a variation of a transmittance spectrum using light transmitted through the bio sensor 1808. Then, at the time point $T_2$, the wavelength-tunable light source 1802 outputs a wavelength from $\lambda_1$ to $\lambda_2$ repeatedly in response to the control of the wavelength light source regulator 1801 until $\lambda_f$ (that is, when a measurement wavelength is saturated according to an antigen-antibody immune reaction) as described in FIG. 12 is obtained. The optical power measurer 1810 measures a biosensor 1808 using only the wavelength light source 1802.

According to the configuration of the embodiments, an error generated when a measurement start time point is not exactly detected in an optical biosensor reader can be reduced. Accordingly, more exact measured values can be obtained compared to typical optical biosensor readers.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A measurement device comprising:
a sensor accepting a sample;
a wavelength-tunable light source irradiating wavelength-tunable light to detect a reaction of the sensor;
an additional light source irradiating wavelength-fixed light to detect an initial time of the reaction in an off-state of the wavelength-tunable light source, wherein a variation of a transmittance spectrum is measured using the wavelength-tunable light source in an off-state of the additional light source after measuring the initial time of the reaction;
a coupler combining the wavelength-tunable light source and the additional light source and irradiating the combined input light on the sensor; and
an optical power measurer detecting the reaction of the sensor from an output light transmitted through or reflected by the sensor.

2. The measurement device of claim 1, wherein the additional light source has optical power varied with time.

3. The measurement device of claim 1, wherein the wavelength-tunable light source has optical power constant with time.

4. The measurement device of claim 1, further comprising a wavelength light source regulator controlling a wavelength output of the wavelength-tunable light source.

5. The measurement device of claim 1, further comprising a light source regulator modulating an output power of the additional light source into a sine wave or a square wave.

6. The measurement device of claim 1, further comprising a signal processing unit separating a component of the additional light source from a result of the detection of the optical power measurer.

7. The measurement device of claim 1, wherein the sensor comprises a specific antibody for detecting the reaction of the sensor.

8. The measurement device of claim 7, wherein the sample comprises an antigen reacting with the antibody.

9. The measurement device of claim 1, further comprising a lens changing the combined input light into parallel light.

10. The measurement device of claim 1, wherein the sensor comprises an optical biosensor.

11. A measurement device comprising:
a sensor accepting a sample;
a light source irradiating light to the sensor;
a beam splitter dividing output light transmitted through or reflected by the sensor into two branches;
a spectroscope detecting a reaction of the sensor by receiving one branched output light from the beam splitter; and
an optical power measurer detecting an initial reaction time of the sensor by receiving the other branched output light from the beam splitter,
wherein the light source comprises a wavelength-tunable light source and a wavelength-fixed light source, and a variation of a transmittance spectrum is measured using the wavelength-tunable light source in an off-state of the wavelength-fixed light source after measuring the initial reaction time of the sensor.

12. The measurement device of claim 11, wherein the optical power measurer comprises an optical filter outputting a wavelength band according to the reaction in the other branched output light.

13. The measurement device of claim 11, wherein the wavelength band comprises a wavelength having maximum transmittance or reflectance and wavelengths adjacent thereto.

14. The measurement device of claim 11, wherein the optical filter comprises a band pass filter.

15. The measurement device of claim 11, wherein the sensor comprises an optical biosensor.

* * * * *